United States Patent
Fransson

(10) Patent No.: US 8,995,676 B2
(45) Date of Patent: Mar. 31, 2015

(54) HEARING PROTECTOR

(75) Inventor: Henrik Fransson, Vallentuna (SE)

(73) Assignee: 3M Svenska AB, Sollentuna (SE)

(*) Notice: Subject to any disclaimer, the term of this patent is extended or adjusted under 35 U.S.C. 154(b) by 496 days.

(21) Appl. No.: 12/933,607

(22) PCT Filed: Mar. 23, 2009

(86) PCT No.: PCT/SE2009/000153
§ 371 (c)(1),
(2), (4) Date: Sep. 20, 2010

(87) PCT Pub. No.: WO2009/120130
PCT Pub. Date: Oct. 1, 2009

(65) Prior Publication Data
US 2011/0019834 A1 Jan. 27, 2011

(30) Foreign Application Priority Data
Mar. 26, 2008 (SE) ...................... 0800675

(51) Int. Cl.
A61F 11/06 (2006.01)
G10K 11/16 (2006.01)
(Continued)

(52) U.S. Cl.
CPC ............ *H04R 1/1083* (2013.01); *G10K 11/178* (2013.01); *A61F 2011/145* (2013.01); *G10K 2210/1081* (2013.01)
USPC ............. 381/72; 381/56; 381/71.1; 381/71.2; 381/71.6

(58) Field of Classification Search
CPC . A61F 2011/145; A61F 11/08; H04R 1/1083; G10K 11/1788; G10K 11/178; G10K 11/1784; G10K 2210/1081; G10K 2210/3023; G10K 2210/3045; G10K 2210/511

USPC .......... 381/72, 74, 56, 71.1, 71.2, 71.6, 71.13
See application file for complete search history.

(56) References Cited

U.S. PATENT DOCUMENTS

| 3,087,028 A | 4/1963 | Bonnin |
| 3,306,991 A | 2/1967 | Wood |

(Continued)

FOREIGN PATENT DOCUMENTS

| DE | 10117704 | 6/2001 |
| EP | 0465971 A2 | 1/1992 |

(Continued)

OTHER PUBLICATIONS

Rafaely et al., "Combined feedback-feedforward active noise-reducing headset—The effect of the acoustics on broadband performance", Jounal of Acoustic Society of America, Sep. 2002.*

(Continued)

Primary Examiner — Vivian Chin
Assistant Examiner — Douglas Suthers
(74) Attorney, Agent, or Firm — Kristofor L. Storvick

(57) ABSTRACT

A hearing protector comprises two protective muffs (1) with passive noise damping, a microphone (3) disposed in at least the one protective muff (1) and connected to an analog and a digital signal processing device (5 and 7, respectively), the signal processing devices (5, 7) being connected to loudspeakers (4) disposed interiorly in the protective muffs (1) for extinguishing interior noise in the protective muffs (1). The analog signal processing device is rehearsed for processing non-repeatable noise, while the digital signal processing device is rehearsed for processing repeatable noise. According to the invention, a further microphone (8) is disposed outside the passive noise damping and is connected to the digital signal processing device for tracing and locking onto repeatable noise.

13 Claims, 1 Drawing Sheet

(51) Int. Cl.
*H03B 29/00* (2006.01)
*H04R 29/00* (2006.01)
*H04R 1/10* (2006.01)
*G10K 11/178* (2006.01)
*A61F 11/14* (2006.01)

(56) References Cited

U.S. PATENT DOCUMENTS

| | | | |
|---|---|---|---|
| 3,394,226 | A | 7/1968 | Andrews, Jr. |
| 3,529,102 | A | 9/1970 | Rosenstand |
| 3,869,584 | A | 3/1975 | Wilde |
| 3,890,474 | A | 6/1975 | Glicksberg |
| 3,947,646 | A | 3/1976 | Saito |
| 3,952,158 | A | 4/1976 | Kyle et al. |
| 4,025,734 | A | 5/1977 | Alcupis |
| 4,064,362 | A | 12/1977 | Williams |
| 4,087,653 | A | 5/1978 | Frieder, Jr. et al. |
| 4,088,849 | A | 5/1978 | Usami |
| 4,150,262 | A | 4/1979 | Cno |
| 4,302,635 | A | 11/1981 | Jacobsen |
| 4,455,675 | A | 6/1984 | Bose |
| 4,588,868 | A | 5/1986 | Bertagna |
| 4,644,581 | A | 2/1987 | Sapiejewski |
| 4,654,871 | A * | 3/1987 | Chaplin et al. ............ 381/72 |
| 4,833,719 | A | 5/1989 | Carme et al. |
| 4,867,149 | A | 9/1989 | Falco |
| 4,887,693 | A | 12/1989 | Plice |
| 4,928,311 | A | 5/1990 | Trompler |
| 4,985,925 | A | 1/1991 | Langberg et al. |
| 5,125,032 | A | 6/1992 | Meister et al. |
| 5,251,263 | A | 10/1993 | Andrea et al. |
| 5,404,577 | A | 4/1995 | Zuckerman |
| 5,450,496 | A | 9/1995 | Burris |
| 5,511,127 | A * | 4/1996 | Warnaka ............... 381/71.5 |
| 5,550,923 | A | 8/1996 | Hotvet |
| 5,631,965 | A | 5/1997 | Chang et al. |
| 5,675,658 | A * | 10/1997 | Brittain .................. 381/72 |
| 5,701,355 | A | 12/1997 | Brannan |
| 5,870,483 | A | 2/1999 | Wong |
| 6,412,593 | B1 | 7/2002 | Jones |
| 6,463,157 | B1 | 10/2002 | May |
| 6,567,525 | B1 | 5/2003 | Sapiejewski |
| 6,574,345 | B1 | 6/2003 | Huang |
| 6,597,792 | B1 | 7/2003 | Sapiejewski |
| 6,631,279 | B2 | 10/2003 | Rivera |
| 6,704,428 | B1 | 3/2004 | Wurtz |
| 6,748,087 | B1 | 6/2004 | Jones |
| 6,801,629 | B2 | 10/2004 | Brimhall |
| 6,965,681 | B2 | 11/2005 | Almqvist |
| 6,970,571 | B2 | 11/2005 | Knorr |
| 7,245,735 | B2 | 7/2007 | Han |
| 7,308,106 | B2 | 12/2007 | Vaudrey |
| 7,327,850 | B2 | 2/2008 | Crump |
| 7,391,878 | B2 | 6/2008 | Liao |
| 7,664,282 | B2 | 2/2010 | Urso |
| 8,054,985 | B2 | 11/2011 | Doty |
| 2001/0046304 | A1 | 11/2001 | Rast |
| 2002/0080979 | A1 | 6/2002 | Brimhall et al. |
| 2002/0080987 | A1 | 6/2002 | Almqvist |
| 2003/0223612 | A1 | 12/2003 | Knorr et al. |
| 2004/0125976 | A1 | 7/2004 | Reneker |
| 2004/0258253 | A1 | 12/2004 | Wurtz |
| 2005/0013447 | A1 * | 1/2005 | Crump et al. ............ 381/71.6 |
| 2005/0220318 | A1 | 10/2005 | Han |
| 2005/0254665 | A1 | 11/2005 | Vaudrey et al. |
| 2007/0076897 | A1 | 4/2007 | Philipp |
| 2007/0183606 | A1 | 8/2007 | Doty |
| 2007/0274529 | A1 | 11/2007 | Nordin et al. |
| 2008/0011084 | A1 | 1/2008 | Von Dach et al. |

FOREIGN PATENT DOCUMENTS

| | | |
|---|---|---|
| EP | 0967592 | 12/1999 |
| EP | 1629808 A1 | 3/2006 |
| GB | 1160431 A | 8/1969 |
| GB | 1289993 A | 9/1972 |
| GB | 2 441 835 A | 3/2008 |
| GB | 2445984 A | 7/2008 |
| WO | WO 87/04065 | 7/1987 |
| WO | WO 91/07153 | 5/1991 |
| WO | WO 96/08004 | 3/1996 |
| WO | WO 97/28742 A1 | 8/1997 |
| WO | WO 02/17838 | 3/2002 |
| WO | WO 2005/051255 | 6/2005 |
| WO | WO 2006/118514 | 11/2006 |
| WO | WO 2008/099137 | 8/2008 |
| WO | WO 2008/113822 | 9/2008 |

OTHER PUBLICATIONS

Boaz Rafely, *Active Noise Reducing Headset—An Overview*, 2001 International Congress and Exhibition on Noise Control Engineering, The Hague, The Netherlands, Aug. 27-30, 2001.

International Search Report for PCT/SE2009/000153 prepared by the Swedish patent Office, dated Jun. 18, 2009.

Supplementary European Search Report for EP 09725543.4, mailed on Jan. 20, 2015, 3 pp.

* cited by examiner

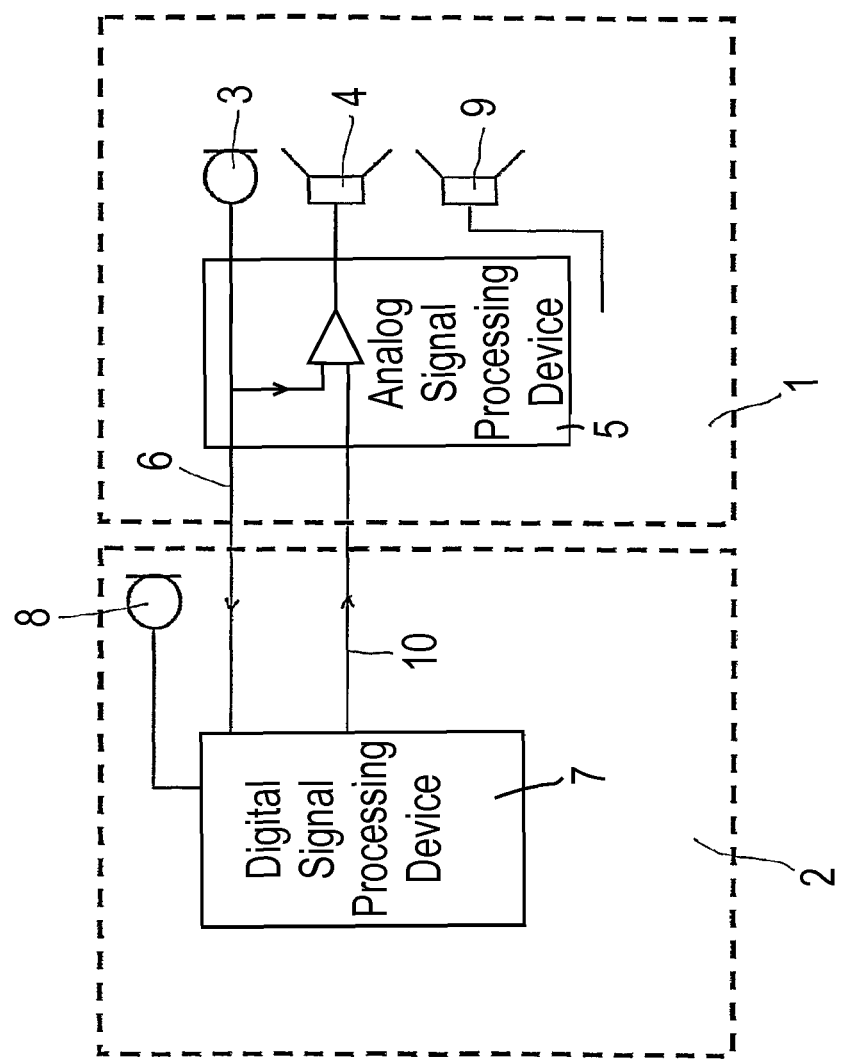

HEARING PROTECTOR

CROSS REFERENCE TO RELATED APPLICATIONS

This application is a national stage filing under 35 U.S.C. 371 of PCT/SE2009/000153, filed Mar. 23, 2009, which claims priority to Swedish Application No. 0800675-1, filed Mar. 26, 2008, the disclosure of which is incorporated by reference in its/their entirety herein.

TECHNICAL FIELD

The present invention relates to a hearing protector which comprises a protective muff provided for each ear of a wearer, with at least a certain passive noise damping, a microphone disposed interiorly in the protective muff and connected to an analog signal processing device and a digital signal processing device, the signal processing devices being connected to at least one loudspeaker disposed interiorly in the muff for emitting sound for extinguishing noise in the protective muff, and the analog signal processing device being substantially rehearsed for processing non-repeatable noise while the digital signal processing device is substantially rehearsed for processing repeatable noise.

BACKGROUND ART

Hearing protection with active noise damping is previously known in the art where there is disposed, interiorly in a protective muff, a microphone, a loudspeaker and a signal processing device, often of analog type. The protective muff has, in a traditional manner, a passive noise damping, which primarily damps out noise of higher frequencies, down to a region in the order of magnitude of 200 to 300 Hz. The signal processing device is formed in such a manner that the input signal from the microphone is phase reversed and its amplitude is adapted so that the signal emitted from the loudspeaker extinguishes the noise interiorly in the protective muff.

The analog signal processing device is rapid and consequently handles random, non-repeatable with good effect.

It is also previously known in the art to employ digital signal processing for noise damping. This signal processing is however slower than the analog processing, for which reason the digital signal processing is better suited for regularly recurring, repeatable noise such as engine noise, propeller noise and the like. Since the digital signal processing can be formed in such a manner that it seeks out the regularly recurring noise, extinguishing this noise can be made more effective than is possible with analog signal processing.

Combinations of analog and digital signal processing are also known in the art and are based on the use of the microphone interiorly in the protective muff.

That sound which impinges on the microphone disposed interiorly in the protective muff has passed through the passive noise damping, and also the analog and digital signal processing, for which reason the repeatable noise is damped and can be masked by the random, non-repeatable noise. This implies problems for the digital signal processing to trace and follow the repeatable noise, so that this can also be extinguished with good effect.

A general problem inherent in prior art technology is that the forming and fine-tuning as a rule takes place on the basis of some measurement norm or standard, e.g. A-weighted level, NRR (Noise Reduction Rating) etc. This implies that no, or slight, attention has been paid to 'perceived residual spectrum' interiorly in the hearing protection. Thus, low frequency noise has often been disregarded, and this noise may be extremely fatiguing and mask radio sound, i.e. communications, even though such sound does not give an indication on A-weighted measurements.

Problem Structure

The present invention has for its object to design the hearing protector intimated by way of introduction such that it obviates the drawbacks inherent in the prior art technology. In particular, the present invention has for its object to design the hearing protector such that it is capable, with very great effect, of identifying and extinguishing also repeatable noise in the protective muff. The present invention also has for its object to design the hearing protector so that it continuously adapts to its ambient surrounding noise and gives a subjectively good noise damping.

Solution

The objects forming the basis of the present invention will be attained if the hearing protection intimated by way of introduction is characterised by a second microphone disposed outside the passive noise damping and connected to the digital signal processing device.

BRIEF DESCRIPTION OF THE ACCOMPANYING DRAWING

The present invention will now be described in greater detail hereinbelow, with reference to the accompanying Drawing which shows a simplified, outline diagram of the subject matter of the present invention.

DESCRIPTION OF PREFERRED EMBODIMENT

In the accompanying Drawing, reference numeral 1 (inside the rectangle shown by broken lines) relates to the interior of a protective muff with at least certain passive noise damping. Reference numeral 2 relates to a space on the protective muff but outside its passive noise damping. The passive noise damping is designed to substantially damp higher frequencies down to frequencies in the region of 200 to 300 Hz. Interiorly in the protective muff 1, there is disposed a microphone 3, a loudspeaker 4 and an analog signal processing device 5. This may also be disposed outside the passive noise damping. The microphone 3 emits an input signal to the analog signal processing device 5, which in its simplest embodiment phase reverses the signal and amplifies it sufficiently for the loudspeaker 4, which is driven by the analog signal processing device 5, to be able to emit a sound which extinguishes the noise prevailing interiorly in the protective muff 1. In such instance, the analog signal processing device 5 is designed in such a manner that it gives priority to the extinguishing of low frequency noise, preferably noise below approx. 200 to 300 Hz.

It will be apparent from the Drawing that the microphone 3 is also connected via a lead 6 to a digital signal processing device 7, which purely physically may be disposed on the outside of the passive noise damping of the protective muff and interiorly in an enclosure 2 provided for this purpose. The digital signal processing device is designed to trace and analyse regularly recurring noise, for example engine noise or propeller noise in order, via a lead 10 to the analog signal processing device 5 and the loudspeaker 4, to emit a signal which extinguishes such regularly recurring noise interiorly in the protective muff 1.

The noise which the microphone 3 interiorly in the protective muff 1 picks up is a residual noise which remains after the passage of the noise through the passive noise damping. This noise includes both repeatable noise and non-repeatable, random noise, where the repeatable noise may be partly damped out and moreover more or less masked by the random noise. This implies that the digital signal processing device 7 in certain situations may find difficulty in tracing, identifying and analysing the repeatable noise.

According to the present invention, there is disposed on the outside of the passive noise damping of the protective muff 1, a second microphone 8 which is connected to the digital signal processing device. Purely physically, the outer microphone 8 is disposed in an enclosure on the outside of the passive noise damping of the protective muff 1, together with the digital signal processing device 7.

The digital signal processing device 7 is designed in such a manner that, when it comes to tracing and identifying the repeatable noise, priority is given to the outer microphone 8, while the inner microphone 3 provides a feedback and establishes the amplitude and phase of the extinguishing signal which is to be emitted via the loudspeaker 4.

In a further development, the second microphone 8 is disposed to sense whether the total noise level is sufficiently high for active noise damping to do anything positive at all at any given moment. The output signal from the second microphone 8 also contains information about the frequency spectrum and amplitude at different frequencies.

In the digital signal processing device 7, the signal from the second microphone 8 is analysed in respect of frequency components, whereafter sinus tones are synthesized on those frequencies which were discovered. In such instance, the first microphone 3 is used only as feedback in order to finely tune the amplitude and phase of the synthesized tones so that these are phase reversed in relation to the noise in the ear.

According to the present invention, it is also possible to use the output signal of the second microphone 8 for controlling the damping of the analog signal processing device 5 so that this may vary in response to the external noise level.

According to the present invention, it is further possible to cause the second microphone 8 to control the analog signal processing device 5 so that this, in response to the level of the external noise, is deactivated and activated for purposes of saving battery power. It is also possible, after a certain time, to deactivate the entire hearing protection if the external noise has been sufficiently low during a given period of time.

In order to save battery power, the headset can also be deactivated automatically if it has been removed from the head of the wearer during a lengthy period of time. In order to verify whether such is the case, the signals from both of the microphones 3 and 8 are compared. If they are at substantially the same level, the probability is very great that the headset is not in position on a wearer's head.

Yet a further variation of the present invention includes the possibility of electing to reduce the damping for a given desired ambient noise, such as warning signals, whose frequency is known.

In one embodiment, it is possible that the digital signal processing device 7 is totally passive as regards random noise, whereby the analog signal processing device 5 alone accounts for the damping or extinguishing of such noise.

It will further be apparent from the Drawing FIGURE that there may be provided, interiorly in the protective muff 1, yet a further loudspeaker 9, which may be a loudspeaker in a communications radio.

The present invention is not restricted to that described above and shown on the Drawing, many modifications being conceivable without departing from the scope of the appended Claims.

What is claimed is:

1. A hearing protector which comprises:
a protective muff (1) provided for each ear of a wearer, with at least a certain passive noise damping, a microphone (3) disposed interiorly in the protective muff and connected to an analog signal processing device (5) and a digital signal processing device (7), such that the microphone (3) provides a feedback to the digital signal processing device, the signal processing devices being connected to at least one loudspeaker (4) disposed interiorly in the muff for emitting sound for extinguishing noise in the protective muff, and the analog signal processing device being configured to process non-repeatable noise while the digital signal processing device is configured to process repeatable noise, characterized by a second microphone (8) disposed outside the passive noise damping and connected to the digital signal processing device (7), and wherein a signal from the second microphone (8) is analyzed in respect of frequency components over a frequency spectrum of the by the digital signal processing device (7) to create a synthesized digital signal that is comprised of a plurality of sinus tones and that is used to cancel noise within the protective muff.

2. The hearing protector as claimed in claim 1, characterised in that the digital signal processing device (7) is able to give priority to signals from the second microphone (8) to trace and identify repeatable noise.

3. The hearing protector as claimed in claim 1, characterised in that the second microphone (8) is disposed in an enclosure (2) on a protective hood but outside its passive noise damping.

4. The hearing protector as claimed in claim 3, characterised in that the digital signal processing device (7) is disposed in the enclosure (2).

5. The hearing protector as claimed in claim 1, characterised in that the second microphone (8) is disposed to sense whether a total noise level is sufficiently high for the second microphone (8) to engage in active noise canceling.

6. The hearing protector as claimed in claim 1, characterised in that the second microphone (8) controls the analog signal processing device (5).

7. The hearing protector as claimed in claim 1, characterised in that the second microphone (8) is disposed to deactivate the analog signal processing device (5) in response to a level of external noise.

8. The hearing protector as claimed in claim 1, characterized in that the hearing protector is automatically deactivated if the level of external noise has been sufficiently low for a given period of time.

9. The hearing protector as claimed in claim 1, characterised in that the hearing protector is disposed to be automatically deactivated if it has been removed from the head of a wearer for a given length of time.

10. The hearing protector as claimed in claim 1, characterised in that the digital signal processing device (7) is passive with respect to random noise.

11. The hearing protector as claimed in claim 1, characterised in that a second loudspeaker (9) for a communications radio is provided interiorly in the protective muff (1).

12. The hearing protector as claimed in claim 1, wherein amplitude and phase of the synthesized digital signal are tuned to be phase reversed relative to noise within the protective muff.

13. The hearing protector as claimed in claim 1, wherein sinus tones of frequencies can be synthesized to be phase reversed relative to noise in the protective muff.

* * * * *

UNITED STATES PATENT AND TRADEMARK OFFICE
CERTIFICATE OF CORRECTION

| | | |
|---|---|---|
| PATENT NO. | : 8,995,676 B2 | Page 1 of 1 |
| APPLICATION NO. | : 12/933607 | |
| DATED | : March 31, 2015 | |
| INVENTOR(S) | : Henrik Fransson | |

It is certified that error appears in the above-identified patent and that said Letters Patent is hereby corrected as shown below:

Title Page, item (56), under Other Publications
Line 3, delete "jounal" and insert -- journal --.

In the Claims,
Column 4
Claim 1, line 26, after "the" insert -- signal --. (first occurrence)

Signed and Sealed this
First Day of September, 2015

Michelle K. Lee
*Director of the United States Patent and Trademark Office*